US00PP34017P2

(12) United States Plant Patent
Bernuetz

(10) Patent No.: US PP34,017 P2
(45) Date of Patent: Mar. 15, 2022

(54) ***EUPHORBIA* PLANT NAMED 'BONPR 611'**

(50) Latin Name: ***Euphorbia pulcherrima* Willd. ex Klotzsch X *Euphorbia cornastra***
Varietal Denomination: Bonpr 611

(71) Applicant: Andrew Bernuetz, Silverdale (AU)

(72) Inventor: Andrew Bernuetz, Silverdale (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 17/379,300

(22) Filed: Jul. 19, 2021

(51) Int. Cl.
*A01H 5/02* (2018.01)
*A01H 6/38* (2018.01)

(52) U.S. Cl.
USPC ..... Plt./306
CPC ..... *A01H 6/385* (2018.05)

(58) Field of Classification Search
USPC ..... Plt./306
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Euphorbia* plant named 'Bonpr 611', characterized by its relatively compact, upright and mounded plant habit; vigorous growth habit; freely branching habit; inflorescences with purplish pink-colored flower bracts with random very pale purple-colored spots, flecks and sectors; relatively small cyathia; and good post-production longevity.

2 Drawing Sheets

Figure 1:
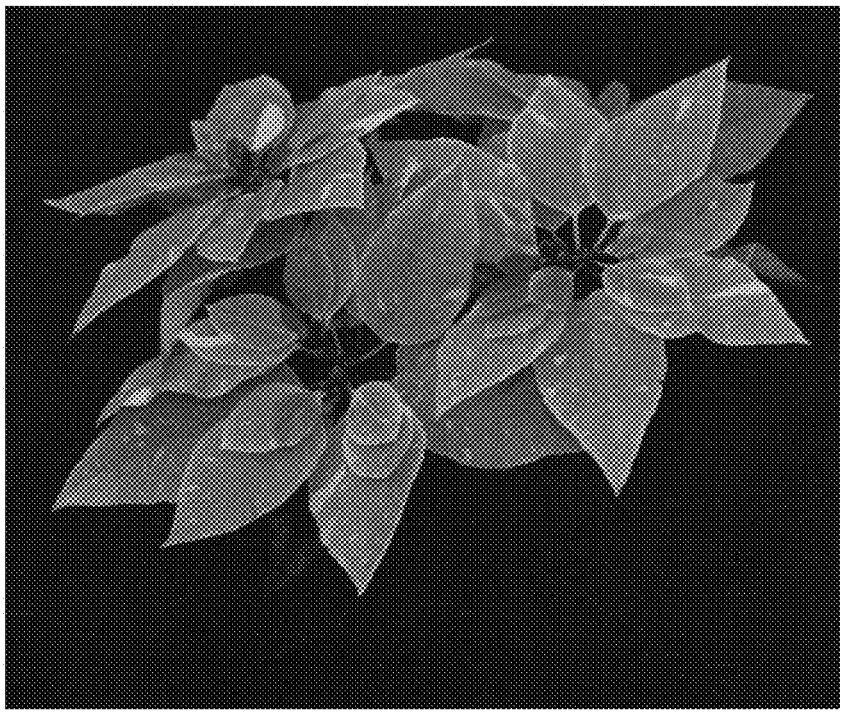

Botanical designation: *Euphorbia pulcherrima* Willd. ex Klotzsch X *Euphorbia cornastra.*
Cultivar denomination: 'BONPR 611'.

STATEMENT REGARDING PRIOR DISCLOSURES BY THE INVENTOR/APPLICANT & ASSIGNEE

A Japanese Plant Breeder's Rights application for the instant plant was filed by the Assignee of the instant application, Bonza Botanicals Pty., Ltd. of Yellow Rock, New South Wales, Australia on Sep. 24, 2020, application number 34953. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'Bonpr 611'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number 415, not patented. The new *Euphorbia* plant was discovered and selected by the Inventor as a single flowering plant from within a population of plants of the mutation parent selection in a controlled greenhouse environment in Yellow Rock, New South Wales, Australia in June, 2007.

Asexual reproduction of the new *Euphorbia* plant by terminal vegetative cuttings in a controlled greenhouse environment in Yellow Rock, New South Wales, Australia since June, 2007 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpr 611'. These characteristics in combination distinguish 'Bonpr 611' as a new and distinct *Euphorbia* plant:

1. Relatively compact, upright and mounded plant habit.
2. Vigorous growth habit.
3. Freely branching habit.
4. Inflorescences with purplish pink-colored flower bracts with random very pale purple-colored spots, flecks and sectors.
5. Relatively small cyathia.
6. Good post-production longevity.

Plants of the new *Euphorbia* differ primarily from plants of the mutation parent selection in flower bract color as flower bracts of plants of the new *Euphorbia* are purplish pink in color with random very pale purple-colored spots, flecks and sectors whereas flower bracts of plants of the mutation parent selection are light pink in color.

Plants of the new *Euphorbia* can be compared to plants of the *Euphorbia pulcherrima* Willd. ex Klotzsch X *Euphorbia cornastra* 'Bonprilipcom', disclosed in U.S. Plant Pat. No. 21,327. In side-by-side comparisons, plants of the new *Euphorbia* differ primarily from plants of 'Bonprilipcom' in the following characteristics:

1. Plants of the new *Euphorbia* are larger than plants of 'Bonprilipcom'.
2. Plants of the new *Euphorbia* have thicker lateral stems than plants of 'Bonprilipcom'.
3. Plants of the new *Euphorbia* have smaller leaves than plants of 'Bonprilipcom'.
4. Plants of the new *Euphorbia* have smaller flower bracts than plants of 'Bonprilipcom'.
5. Plants of the new *Euphorbia* and 'Bonprilipcom' differ in flower bract color as flower bracts of plants of the new *Euphorbia* are purplish pink in color with random very pale purple-colored spots, flecks and sectors whereas flower bracts of plants of 'Bonprilipcom' are solid pink in color.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet (FIG. 1) is a side perspective view of a typical flowering plant of 'Bonpr 611' grown in a container.

Figure 2:
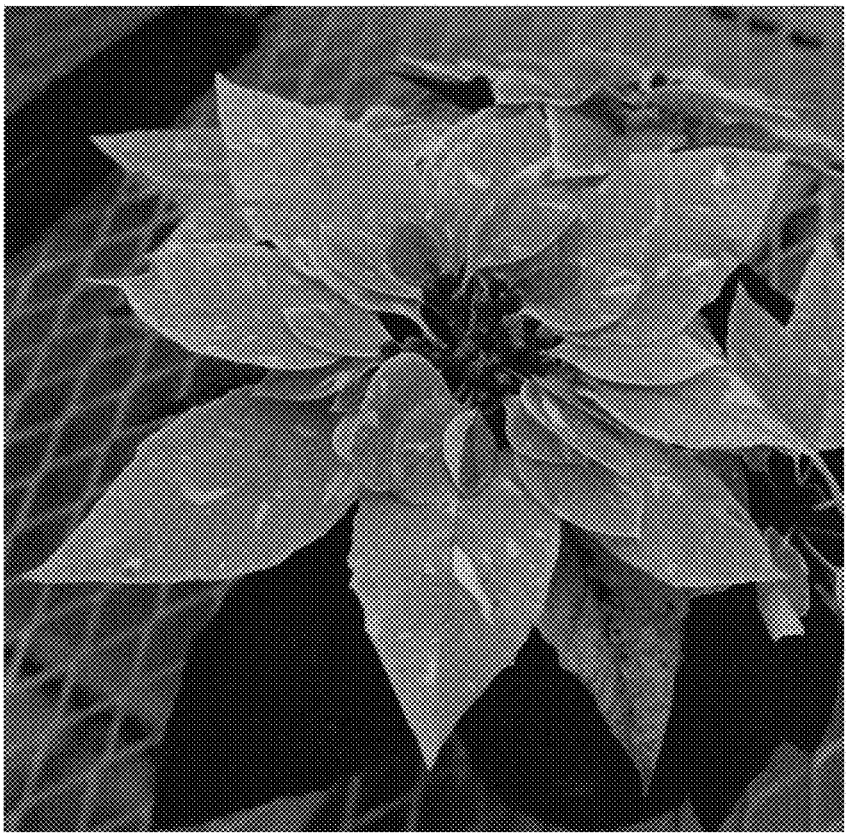

The photograph on the second sheet (FIG. 2) is a close-up view of a typical flowering plant of 'Bonpr 611'.

DETAILED BOTANICAL DESCRIPTION

Plants used in the aforementioned photographs and described herewith in detail were grown during the autumn and early winter in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'Bonpr 611'.

Parentage: Naturally-occurring whole plant mutation of a proprietary selection of *Euphorbia pulcherrima* Willd. ex Klotzsch X *Euphorbia cornastra* identified as code number 415, not patented.

Propagation:

*Type*.—Terminal vegetative cuttings.

*Time to initiate roots, summer*.—About ten days at temperatures about 20° C. to 21° C.

*Time to initiate roots, winter*.—About twelve days at temperatures about 20° C. to 21° C.

*Time to produce a rooted young plant, summer*.—About 24 days at temperatures about 20° C. to 21° C.

*Time to produce a rooted young plant, winter*.—About four weeks at temperatures about 20° C. to 21° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Relatively compact, upright and mounded plant habit; inverted triangle; inflorescences positioned above the foliar plane; vigorous growth habit.

*Plant height*.—About 19 cm.

*Plant diameter or spread*.—About 25.4 cm.

*Lateral branch description*.—Branching habit: Freely branching habit, about 4.2 lateral branches develop per plant. Length: About 8.5 cm. Diameter: About 3.9 mm. Internode length: About 1.4 cm. Aspect: Mostly upright to somewhat outward. Strength: Strong. Texture: Smooth, glabrous. Color: Close to NN137C.

*Leaf description*.—Arrangement: Alternate, simple. Length: About 6.9 cm. Width: About 4.4 cm. Shape: Lanceolate. Apex: Acute. Base: Rounded. Margin: Serrate, occasionally with few shallow lobes; slightly undulate. Venation pattern: Pinnate, reticulate. Texture and luster, upper surface: Smooth, glabrous; matte. Texture and luster, lower surface: Rough, sparsely pubescent; matte. Color: Developing leaves, upper surface: Close to 137A. Developing leaves, lower surface: Close to 137C. Fully developed leaves, upper surface: Close to 139A; venation, close to 141C. Fully developed leaves, lower surface: Close to 138B; venation, close to 143C. Petioles: Length: About 2 cm. Diameter: About 1.7 mm. Texture, upper and lower surfaces: Sparsely pubescent. Color, upper surface: Close to 138A, variably tinged with close to 64A. Color, lower surface: Close to 138A, variably tinged with close to 137D.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about four inflorescences develop per plant.

*Inflorescence diameter*.—About 16.4 cm.

*Inflorescence height*.—About 4.1 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 50 days under natural season or photoinductive conditions in Japan.

*Post-production longevity*.—Good post-production longevity; plants of the new *Euphorbia* maintain good substance and bract color for about eight weeks.

*Flower bracts*.—Quantity per inflorescence: About twelve. Length: About 3.6 cm. Width: About 2.2 cm. Shape: Elliptic. Apex: Acute. Base: Obtuse. Margin: Entire with occasional irregular serrations; slightly undulate. Texture, upper and lower surfaces: Smooth, glabrous. Aspect: Mostly horizontal. Venation pattern: Pinnate, reticulate. Color: Transitional bracts, upper surface: Random sectors and areas, close to 131B and N66C; towards the apex, close to 135C. Transitional bracts, lower surface: Random sectors and areas, close to 135 C and 69C; towards the margins, close to 135C. Developing bracts, upper surface: Close to N57A. Developing bracts, lower surface: Close to N57B. Fully expanded bracts, upper surface: Close to 68A; random spots, flecks and sectors, close to 69D; venation, close to 67D. Fully expanded bracts, lower surface: Close to 63C; venation, close to 143D. Flower bract petioles: Length: About 5 mm. Diameter: About 1.4 mm. Texture, upper and lower surfaces: Sparsely pubescent. Color, upper and lower surfaces: Close to 68A and 143D.

*Cyathia*.—Quantity per corymb: About 16. Diameter of cyathia cluster: About 2.3 cm. Height, individual cyathium: About 5.4 mm. Diameter, individual cyathium: About 5.2 mm. Shape, individual cyathium: Globose. Color: Distally, close to 59B and proximally, close to 143C. Nectaries: Quantity per cyathium: One. Size: About 2.2 mm by 3.3 mm. Texture: Smooth, glabrous. Color: Close to N144B.

*Peduncles*.—Length: About 3.4 mm. Diameter: About 2 mm. Texture, upper and lower surfaces: Smooth, glabrous. Aspect: Mostly upright. Color, upper and lower surfaces: Close to 143B.

*Reproductive organs*.—Stamens: Quantity per cyathia: Two. Filament length: About 2.9 mm. Filament color: Close to 63A. Anther size: About 0.6 mm by 1.1 mm. Anther shape: Oblong. Anther color: Close to 160B and 64A. Pollen amount: Sparse. Pollen color: Close to 2A. Pistils: To date, pistil development has not been observed on plants of the new *Euphorbia*.

*Seeds and fruits*.—To date, seed and fruit production has not been observed on plants of the new *Euphorbia*.

Pathogen & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpr 611' as illustrated and described.

* * * * *